(12) United States Patent
Morris et al.

(10) Patent No.: US 9,610,082 B2
(45) Date of Patent: Apr. 4, 2017

(54) APPARATUS AND METHOD FOR HEART VALVE REPAIR

(71) Applicant: St. Jude Medical, Inc., St. Paul, MN (US)

(72) Inventors: Benjamin E. Morris, Jeffersonville, IN (US); Eric E. Bielefeld, Floyds Knobs, IN (US); Gregory R. Furnish, Louisville, KY (US); Wayne Johnson, Jeffersonville, IN (US); Mark Griffin, Louisville, KY (US)

(73) Assignee: St. Jude Medical, Inc., St. Paul, MN (US)

( * ) Notice: Subject to any disclaimer, the term of this patent is extended or adjusted under 35 U.S.C. 154(b) by 220 days.

(21) Appl. No.: 14/374,748

(22) PCT Filed: Jan. 25, 2013

(86) PCT No.: PCT/US2013/023077
§ 371 (c)(1),
(2) Date: Jul. 25, 2014

(87) PCT Pub. No.: WO2013/112795
PCT Pub. Date: Aug. 1, 2013

(65) Prior Publication Data
US 2014/0371766 A1    Dec. 18, 2014

Related U.S. Application Data

(60) Provisional application No. 61/590,475, filed on Jan. 25, 2012.

(51) Int. Cl.
*A61B 17/122* (2006.01)
*A61B 17/128* (2006.01)
(Continued)

(52) U.S. Cl.
CPC ........ *A61B 17/1227* (2013.01); *A61B 17/068* (2013.01); *A61B 17/0644* (2013.01);
(Continued)

(58) Field of Classification Search
CPC ... A61B 17/068; A61B 17/0682; A61B 17/08; A61B 17/083; A61B 17/10;
(Continued)

(56) References Cited

U.S. PATENT DOCUMENTS

| 5,156,608 A | 10/1992 | Troidl et al. |
| 5,499,991 A | 3/1996 | Garman et al. |

(Continued)

FOREIGN PATENT DOCUMENTS

| AU | 2002300522 B2 | 1/2007 |
| WO | 9620749 A1 | 7/1996 |

(Continued)

OTHER PUBLICATIONS

International Preliminary Report on Patentability for Application No. PCT/US2012/023437 dated Aug. 6, 2013.
(Continued)

*Primary Examiner* — Todd J Scherbel
(74) *Attorney, Agent, or Firm* — Lerner, David, Littenberg, Krumholz & Mentlik, LLP

(57) ABSTRACT

A device 10 for gathering tissue in a patient includes an elongated catheter 14 and a capture assembly 13 at a distal portion of the catheter. The capture assembly has a closed side 18 and a door 20 rotatable between an open condition and a closed condition. The closed side 18 of the capture assembly 13 and the door 20 in the closed condition may collectively define a tissue capturing compartment 19. Movement of the door 20 from the open condition to the closed condition adjacent the tissue may capture a portion 44 of the tissue in the tissue capturing compartment 19. A clip (Continued)

may then be applied from the capture assembly 13 to the captured tissue 44 to hold the tissue substantially in a gathered configuration.

18 Claims, 7 Drawing Sheets

(51) Int. Cl.
 *A61B 17/064* (2006.01)
 *A61B 17/068* (2006.01)
 *A61B 17/00* (2006.01)
(52) U.S. Cl.
 CPC ..... *A61B 17/1285* (2013.01); *A61B 2017/00243* (2013.01); *A61B 2017/00783* (2013.01); *A61B 2017/00867* (2013.01); *A61B 2017/0645* (2013.01); *A61B 2017/0649* (2013.01)
(58) Field of Classification Search
 CPC ..... A61B 17/105; A61B 17/12; A61B 17/122; A61B 17/1227; A61B 17/128; A61B 17/1285; A61B 2017/00243; A61B 2017/081
 See application file for complete search history.

(56) References Cited

U.S. PATENT DOCUMENTS

| | | | |
|---|---|---|---|
| 5,601,573 | A | 2/1997 | Fogelberg et al. |
| 5,741,278 | A | 4/1998 | Stevens |
| 5,749,879 | A | 5/1998 | Middleman et al. |
| 5,921,993 | A | 7/1999 | Yoon |
| 6,258,105 | B1* | 7/2001 | Hart ............... A61B 17/1285 606/142 |
| 6,440,152 | B1 | 8/2002 | Gainor et al. |
| 6,569,182 | B1 | 5/2003 | Balceta et al. |
| 6,626,930 | B1 | 9/2003 | Allen et al. |
| 6,752,813 | B2 | 6/2004 | Goldfarb et al. |
| 6,945,978 | B1 | 9/2005 | Hyde |
| 7,011,669 | B2 | 3/2006 | Kimblad |
| 7,464,712 | B2 | 12/2008 | Oz et al. |
| 7,569,062 | B1 | 8/2009 | Kuehn et al. |
| 7,758,595 | B2 | 7/2010 | Allen et al. |
| 8,777,966 | B2 | 7/2014 | Dale et al. |
| 8,951,285 | B2 | 2/2015 | Sugimoto et al. |
| 2001/0016750 | A1 | 8/2001 | Malecki et al. |
| 2002/0010388 | A1 | 1/2002 | Taylor et al. |
| 2002/0013571 | A1 | 1/2002 | Goldfarb et al. |
| 2002/0035390 | A1 | 3/2002 | Schaldach et al. |
| 2002/0049457 | A1 | 4/2002 | Kaplan et al. |
| 2002/0107531 | A1 | 8/2002 | Schreck et al. |
| 2002/0183768 | A1 | 12/2002 | Deem et al. |
| 2003/0065335 | A1 | 4/2003 | Guido et al. |
| 2003/0093071 | A1 | 5/2003 | Hauck et al. |
| 2003/0120264 | A1* | 6/2003 | Lattouf ........... A61B 17/00234 606/1 |
| 2004/0030335 | A1 | 2/2004 | Zenati et al. |
| 2004/0039442 | A1 | 2/2004 | St. Goar et al. |
| 2004/0087985 | A1 | 5/2004 | Loshakove et al. |
| 2004/0176784 | A1 | 9/2004 | Okada |
| 2004/0181238 | A1 | 9/2004 | Zarbatany et al. |
| 2004/0193185 | A1 | 9/2004 | McBrayer |
| 2005/0004583 | A1 | 1/2005 | Oz et al. |
| 2005/0090837 | A1 | 4/2005 | Sixto et al. |
| 2005/0096671 | A1 | 5/2005 | Wellman et al. |
| 2005/0107871 | A1 | 5/2005 | Realyvasquez et al. |
| 2005/0125011 | A1 | 6/2005 | Spence et al. |
| 2005/0143763 | A1 | 6/2005 | Ortiz et al. |
| 2005/0149072 | A1 | 7/2005 | DeVries et al. |
| 2005/0177176 | A1 | 8/2005 | Gerbi et al. |
| 2005/0251161 | A1 | 11/2005 | Saadat et al. |
| 2006/0009800 | A1 | 1/2006 | Christianson et al. |
| 2006/0089671 | A1 | 4/2006 | Goldfarb et al. |
| 2006/0122633 | A1 | 6/2006 | To et al. |
| 2006/0173422 | A1 | 8/2006 | Reydel et al. |
| 2006/0173473 | A1 | 8/2006 | Bob |
| 2007/0049952 | A1 | 3/2007 | Weiss |
| 2007/0093857 | A1 | 4/2007 | Rogers et al. |
| 2007/0102474 | A1 | 5/2007 | Shelton et al. |
| 2007/0102475 | A1 | 5/2007 | Ortiz et al. |
| 2007/0142846 | A1 | 6/2007 | Catanese et al. |
| 2007/0162056 | A1 | 7/2007 | Gerbi et al. |
| 2007/0197858 | A1 | 8/2007 | Goldfarb et al. |
| 2007/0198032 | A1 | 8/2007 | Ortiz |
| 2007/0225734 | A1 | 9/2007 | Bell et al. |
| 2008/0125796 | A1 | 5/2008 | Graham |
| 2008/0234705 | A1* | 9/2008 | Cropper ............... A61B 17/128 606/157 |
| 2008/0255427 | A1 | 10/2008 | Satake et al. |
| 2008/0294175 | A1 | 11/2008 | Bardsley et al. |
| 2008/0300624 | A1 | 12/2008 | Schwemberger et al. |
| 2008/0319455 | A1 | 12/2008 | Harris et al. |
| 2009/0062852 | A1 | 3/2009 | Marino |
| 2009/0118744 | A1 | 5/2009 | Wells et al. |
| 2009/0125038 | A1 | 5/2009 | Ewers et al. |
| 2009/0149870 | A1 | 6/2009 | Jugenheimer et al. |
| 2011/0054521 | A1 | 3/2011 | Ventura et al. |
| 2011/0077668 | A1 | 3/2011 | Gordon et al. |
| 2011/0087242 | A1 | 4/2011 | Pribanic et al. |
| 2011/0114700 | A1 | 5/2011 | Baxter, III et al. |
| 2011/0230897 | A1 | 9/2011 | Palermo et al. |
| 2011/0313432 | A1 | 12/2011 | Miles et al. |
| 2012/0022532 | A1 | 1/2012 | Garrison |
| 2012/0109159 | A1 | 5/2012 | Jordan et al. |
| 2012/0226291 | A1 | 9/2012 | Malizia et al. |
| 2013/0046332 | A1 | 2/2013 | Jones et al. |
| 2014/0039607 | A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report and Written Opinion for Application No. PCT/US2013/023082 dated Oct. 1, 2013.
International Search Report and Written Opinion for Application No. PCT/US2013/024304 dated Jul. 5, 2013.
International Search Report and Written Opinion for Application No. PCT/US2013/052822 dated Jan. 21, 2014.
International Search Report and Written Opinion for Application No. PCT/US2013/052838 dated Oct. 11, 2013.
International Search Report and Written Opinion for Application No. PCT/US2013/052843 dated Oct. 11, 2013.
International Search Report and Written Opinion for Application No. PCT/US2013/065360 dated Apr. 23, 2014.
International Search Report for Application No. PCT/US2012/023437 dated Apr. 24, 2012.
International Search Report for Application No. PCT/US2013/023077 dated May 14, 2013.

(56) References Cited

OTHER PUBLICATIONS

International Search Report for Application No. PCT/US2013/052832 dated Jan. 15, 2014.

\* cited by examiner

APPARATUS AND METHOD FOR HEART VALVE REPAIR

CROSS-REFERENCE TO RELATED APPLICATION

This application is a national phase entry under 35 U.S.C. §371 of International Application No. PCT/US2013/023077 filed Jan. 25, 2013, published in English, which claims the benefit of the filing date of United States Provisional Patent Application No. 61/590,475 filed Jan. 25, 2012, the disclosures of which are hereby incorporated by reference herein.

BACKGROUND OF THE INVENTION

The present invention is related to tissue repair, and more particularly to devices, systems, and methods for minimally invasive repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve is not properly held in a closed condition. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return to the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse specifically, and for gathering tissue in a patient generally. Among other advantages, the present invention may address one or more of these needs.

BRIEF SUMMARY OF THE INVENTION

Methods and devices for gathering tissue in a patient are disclosed. A method of gathering tissue in a patient may include inserting an elongated device into the patient to a position adjacent the tissue, the device including a capture assembly having a closed side and a door rotatable between an open condition and a closed condition, the closed side and the door in the closed condition collectively defining a tissue capturing compartment. The door may then be moved from the closed condition to the open condition and engaged against the tissue. The door may be closed against the tissue to capture a portion of the tissue inside the tissue capturing compartment, the captured tissue being formed into a gathered configuration. At least one clip from the capture assembly may be applied to the captured tissue so as to hold the captured tissue substantially in the gathered configuration.

The tissue may be a heart valve leaflet. The capture assembly may include a spring element coupled to the door and biased to move the door to the closed condition. The door may include at least one prong projecting therefrom, and the closing step may include grasping the captured tissue with the at least one prong. The door may include a portion with serrations, and the closing step may include grasping the captured tissue with the serrations. The device may include a deployment element attached to the door and operable by a user, and the moving step may include pulling the deployment element to rotate the door to the open condition.

The capture assembly may include first and second doors rotatable between open and closed conditions, and the closing step may include closing the first and second doors against the tissue to capture the portion of the tissue inside the tissue capturing compartment. The clip may be biased to a substantially round condition and may be engaged with the door to hold the clip in an open condition, and the applying step may include releasing the clip from engagement with the door, whereby the clip may move from the open condition to the substantially round condition. The device may include an actuating rod movable relative to the at least one clip, and the applying step may include moving the actuating rod to contact the at least one clip and releasing the at least one clip for application to the captured tissue.

A device for gathering tissue in a patient may include an elongated catheter having a proximal portion and a distal portion and a capture assembly at the distal portion of the catheter. The capture assembly may include a closed side and a door rotatable between an open condition and a closed condition, the closed side and the door in the closed condition collectively defining a tissue capturing compartment. The door may be operable to capture a portion of the tissue in a gathered configuration within the tissue capturing compartment.

The device may also include a spring element coupled to the door and biased to move the door to the closed condition. The door may have one edge rotatably connected to the closed side of the capture assembly and a free edge opposite the one edge. The free edge may include at least one prong projecting therefrom. The free edge may include a plurality of serrations. The device may also include a deployment element attached to the door and extending through the elongated catheter. The capture assembly may include first and second doors rotatable between open and closed conditions. The first and second doors may be operable to capture the portion of the tissue in a gathered configuration within the tissue capturing compartment.

The device may also include at least one clip releasably held in the tissue capturing compartment and adapted to be applied to the captured tissue for holding the captured tissue in the gathered configuration. The clip may be biased to a substantially round condition and may be engaged with the door to hold the clip in an open condition. The clip may have a first end and a second end, and the door may include a slot. The first end of the clip may be engaged in the slot. Movement of the door to the open condition may create a biasing force in the clip tending to move the door to the closed condition.

The device may also include an actuating rod slidably disposed in the tissue capturing compartment. The actuating rod may have a laterally projecting bump, and the clip may be at least partially held in a travel path of the bump. Movement of the bump through the travel path may cause the bump to release the clip for application to the captured tissue. The bump may have an oval cross-section, and a portion of the actuating rod adjacent the bump may have a round cross-section that is smaller than the oval cross-section in at least one direction.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
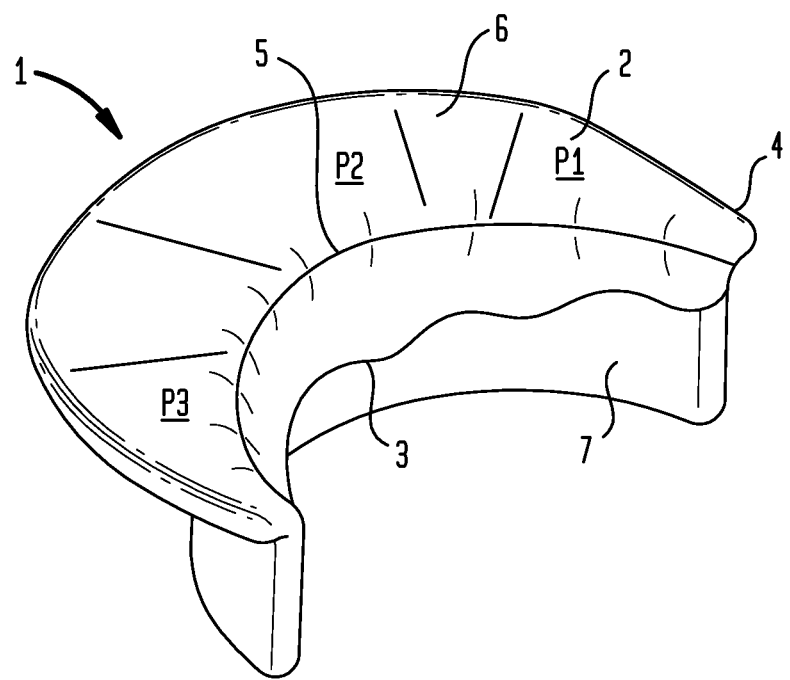
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3. Chordae tendineae 8 (FIG. 3) may connect the lower portion 7 of the posterior leaflet 2 to the papillary muscles of the left ventricle 9.

Figure 2A:
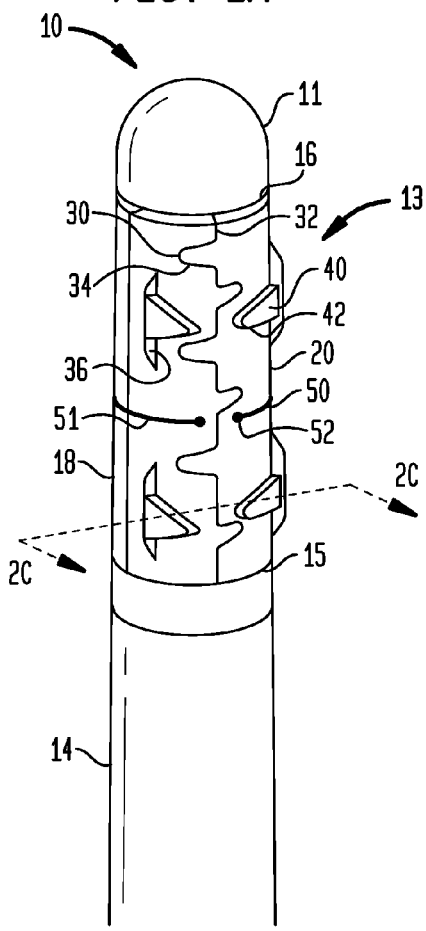
FIG. 2A is a perspective view of the distal portion of one embodiment of a device for gathering tissue of a heart valve leaflet, shown with the doors in the fully closed condition.
Figure 2B:
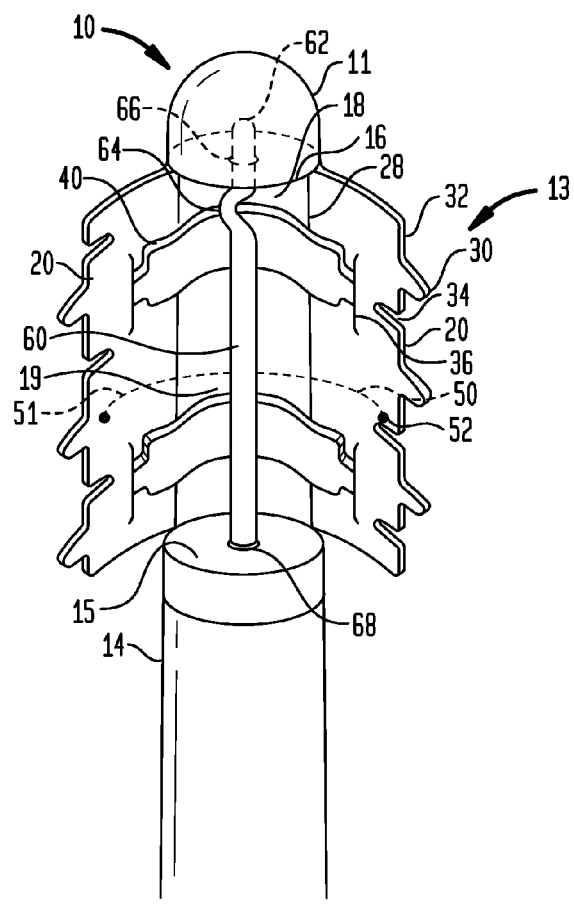
FIG. 2B is a perspective view of the distal portion of the device of FIG. 2A, shown with the doors in the fully open condition.
Figure 2C:
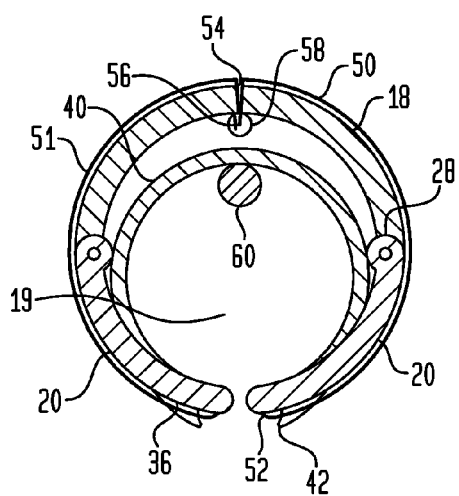
FIG. 2C is a cross-sectional view of the device of FIG. 2A, taken along line 2C-2C of FIG. 2A.

Referring to FIGS. 2A-2C, an exemplary device 10 for gathering heart valve leaflet tissue includes an elongated catheter 14 adapted to be inserted through the apex of a human heart so that a capture assembly 13 at a distal portion of the catheter may reach the patient's mitral valve 1 for repair thereof. The capture assembly 13 preferably has an outer profile and cross-sectional shape similar to that of the catheter 14.

The capture assembly 13 includes a proximal end wall 15, a distal end wall 16, a closed side 18 extending between the proximal and distal end walls, and a pair of hinged doors 20. An atraumatic tip 11 is positioned at the distal end of the capture assembly 13. The capture assembly 13 may be made of one or more echogenic materials so as to be more easily visualized inside a patient using three-dimensional echocardiography.

Each door 20 is rotatably coupled to the closed side 18 at an inner longitudinal edge 28 of the door. As shown in FIGS. 2A-2C, each door 20 may be coupled to the closed side 18 by a hinge that includes a pin extending through apertures in the door and the closed side, but the invention contemplates any other coupling mechanism that allows the doors 20 to be rotatably coupled to the closed side, such as a living hinge.

The doors 20 are rotatable relative to the closed side 18 of the capture assembly 13 between a closed condition shown in FIG. 2A and a fully open condition shown in FIG. 2B. A free longitudinal edge 32 of each door 20 may include prongs 30 adapted to engage with corresponding recesses 34 in the free longitudinal edge 32 of the opposite door when the doors are in the closed condition. In the closed condition of the doors 20, a tissue capturing compartment 19 is defined between the doors and the closed side 18 of the capture assembly 13.

The capture assembly 13 further includes one or more clips 40, the ends of which are engaged in corresponding slots 36 in the doors 20. The ends of each clip 40 may be formed with a prong 42 adapted to embed in the leaflet tissue when the clip is deployed. The clips 40 may be made of a memory metal and may be biased to curl into a substantially round configuration. When the ends of the clips 40 are engaged in the slots 36, this biasing force biases the doors 20 to the closed condition.

A deployment wire 50 for opening the doors 20 may extend through the catheter 14 from a proximal end connected to an actuating mechanism (not shown) located outside of the patient's body, and through the proximal end wall 15 of the capture assembly 13 into the tissue capturing compartment 19. The deployment wire 50 may then travel through a containment tube 58 positioned adjacent the inside surface of the closed side 18 of the capture assembly 13, and through an aperture 54 in the closed side to the exterior of the capture assembly. The distal end of the deployment wire 50 may have two arms 51 that wrap circumferentially around the outside of the closed side 18 of the capture assembly 13 and attach to the two doors 20 at attachment locations 52 near the free edge 32 of each door. As will be explained below, movement of the deployment wire 50 in the proximal direction moves the doors 20 from the closed condition to the open condition.

Figure 6:
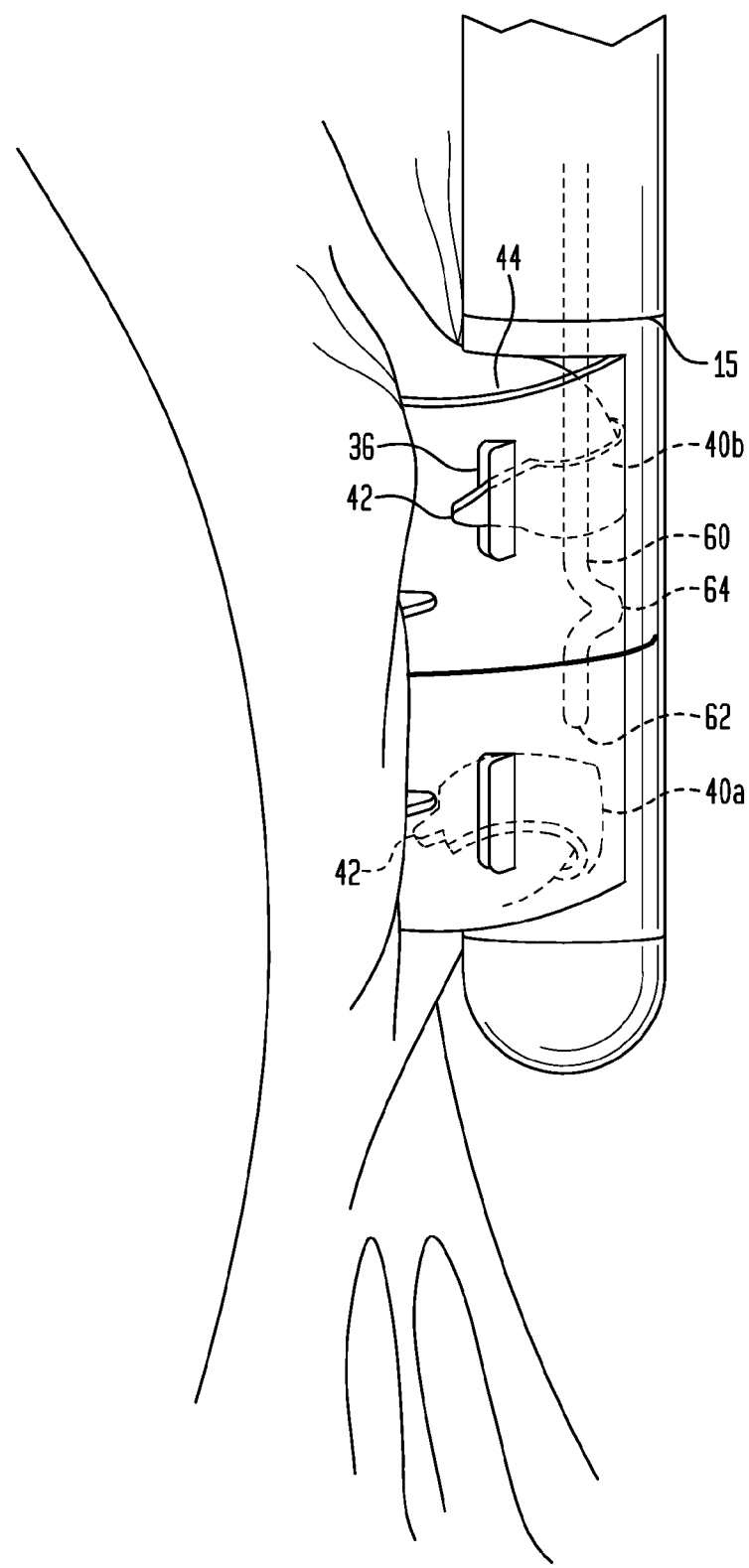

An actuation rod 60 for releasing the clips 40 may extend through the catheter 14 from a proximal end connected to an actuating mechanism (not shown) located outside of the patient's body, and through an aperture 68 in the proximal end wall 15 of the capture assembly 13 into the tissue capturing compartment 19. The actuation rod 60 may be bent to define a bump 64 that curves laterally away from the longitudinal axis of the actuation rod. The actuation rod 60 is slidable between an initial position with its distal end 62 extending through an aperture 66 in the distal end wall 16 and into the atraumatic tip 11 (FIG. 2B), and a deployed position with its distal end located within the tissue capturing compartment 19. An example of a partially-deployed position of the actuation rod 60 is shown in FIG. 6. The bump 64 is adapted to contact the clips 40 when the actuation rod 60 is slid proximally within the compartment 19.

To use the device 10 for gathering heart valve leaflet tissue, a user may first pull the deployment wire 50 proximally to open the doors 20. The clips 40 may then be loaded into the tissue capturing compartment 19 around the actuation rod 60, such that each clip is located between the actuation rod and the closed side 18 of the capture assembly 13, with the prongs 42 of each clip engaged in the corresponding slots 36 in the doors 20. After the clips 40 have been loaded into the tissue capturing compartment 19, the deployment wire 50 may be released, such that the biasing force exerted by the clips will pull the doors 20 into the closed condition.

Figure 3:
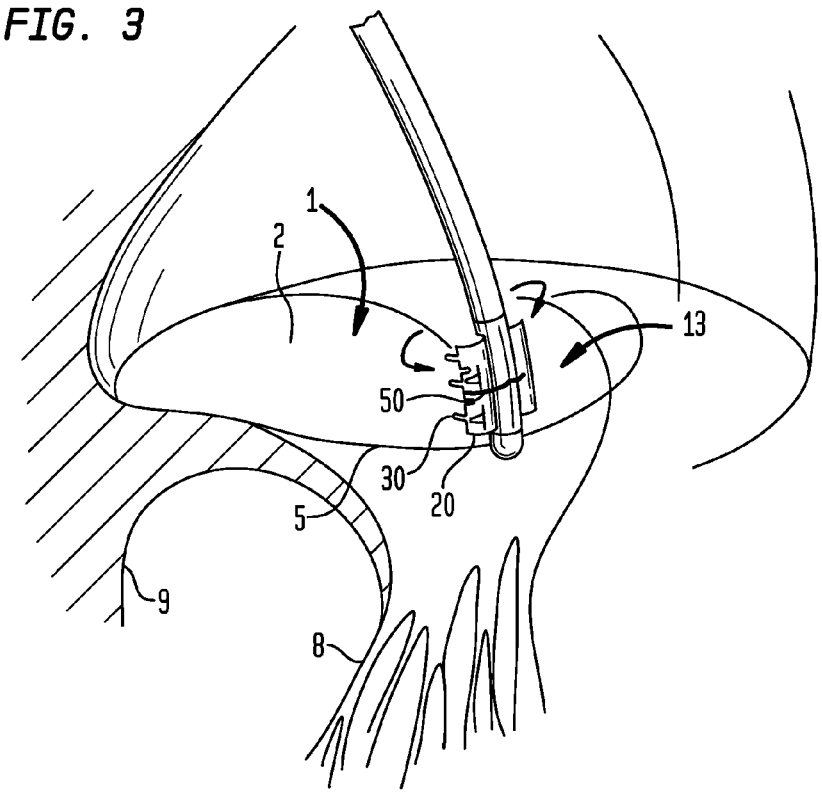
FIGS. 3, 4, 5A, 6, and 7 are diagrammatic views showing the steps of operating the device of FIG. 2A for gathering of heart valve leaflet tissue and applying clips to same.

The device 10 may then be inserted into the patient and advanced until the capture assembly 13 is located adjacent the mitral valve, preferably using a transseptal approach. That is, the device 10 may be advanced from the femoral vein through the iliac vein, the inferior vena cava, and the right atrium, and across the septum wall into the left atrium, until the capture assembly 13 extends between the posterior leaflet 2 and the anterior leaflet 3 of the mitral valve 1, as shown in FIG. 3. This route requires the least amount of bending or turning and provides the most direct route to the mitral valve leaflets. Minimizing the number of turns may facilitate the rotational control of the capture assembly 13. If the capture assembly 13 includes echogenic materials, it may be guided to a position against a leaflet near the coaption line 5 using the assistance of three-dimensional echocardiography.

Once the capture assembly 13 has been positioned near the coaption line 5, the user may pull the deployment wire 50 proximally to move the doors 20 to the fully open condition. To keep the doors 20 open, the deployment wire 50 may be temporary locked relative to the closed side 18 of the capture assembly 13, for example, using a locking feature of a control handle (not shown) located at the proximal end of the catheter 14.

Figure 4:
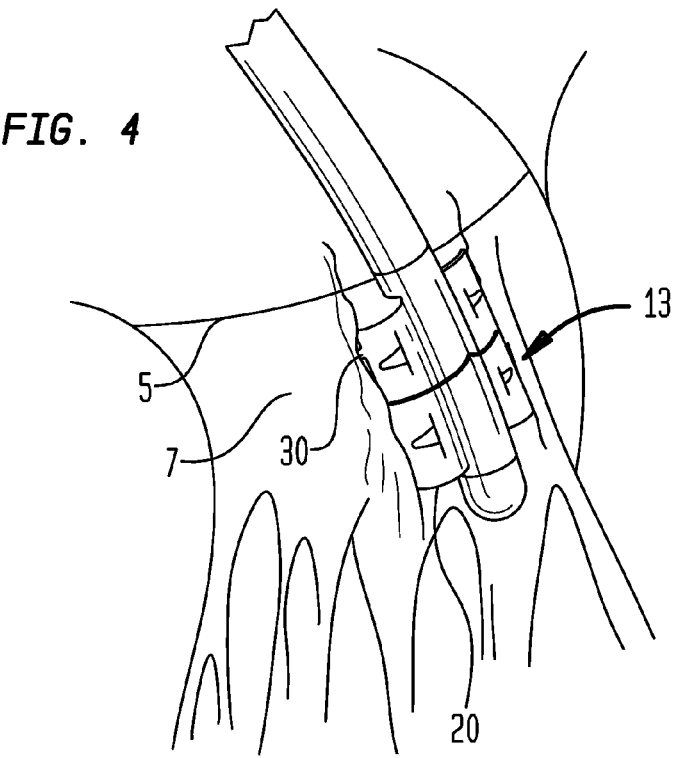

Referring to FIG. 4, with the doors 20 open, the capture assembly 13 may be positioned adjacent the lower portion 7 of the posterior leaflet 2 so that the exposed tissue capturing compartment 19 faces the posterior leaflet. The capture assembly 13 may then be pressed against the lower portion 7 of the posterior leaflet 2 to engage the prongs 30 of the doors 20 in the tissue of the posterior leaflet.

Figure 5A:
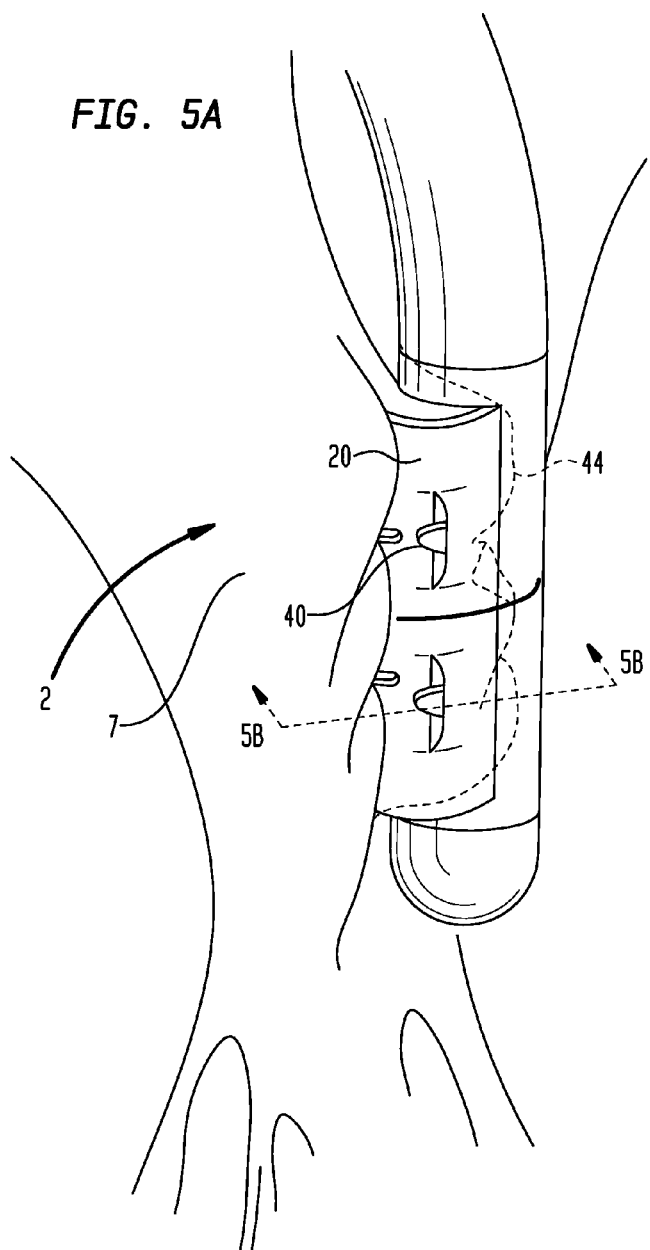
Figure 5B:
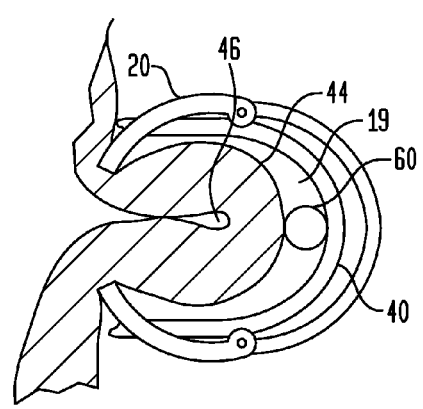
FIG. 5B is a cross-sectional view of the device and gathered tissue, taken along line 5B-5B of FIG. 5A.

Subsequently, the user may release the deployment wire 50, so that the clips 40 are free to begin to curl into a substantially round configuration according to their bias, thereby closing the doors 20 against the tissue of the posterior leaflet 2 until the doors attain the partially open condition shown in FIGS. 5A and 5B. As the doors 20 close, the prongs 30 in the longitudinal edges 32 of the doors may grasp and/or piece the leaflet tissue, pulling it toward the compartment 19. When the doors 20 are in the partially open condition and engaged with the tissue of the posterior leaflet 2, some of the tissue of the posterior leaflet will be captured inside of the tissue capturing compartment 19 and within the diameter of the clips 40. This captured tissue 44 may form a pleat 46 extending substantially along the longitudinal axis of the tissue capturing compartment 19.

Referring to FIG. 6, the user may then release the clips 40 into engagement with the captured tissue 44 by sliding the actuation rod 60 proximally within the compartment 19. As the actuation rod 60 slides proximally, the bump 64 first contacts a distal clip 40a. The bump 64 provides a force in a lateral direction transverse to the longitudinal axis of the compartment 19, thereby forcing the distal clip 40a toward the closed side 18 of the compartment. As the clip 40a is displaced, the prongs 42 of the clip disengage from the slots 36. Only a small transverse movement of each clip 40 is required to disengage the prongs 42 from the corresponding slots 36. Once the clip 40a is disengaged from the slots 36, the clip is free to continue to curl into a substantially round configuration according to its bias, and the prongs 42 of the clip engage and may become embedded in the captured tissue 44 on either side of the pleat 46.

After the distal clip 40a has been applied to the captured tissue 44, the user may slide the actuation rod 60 further proximally, thereby disengaging a proximal clip 40b from the slots 36 and causing the prongs 42 of the proximal clip to engage and possibly embed in the captured tissue 44 in the same manner as the distal clip 40a.

Figure 7:
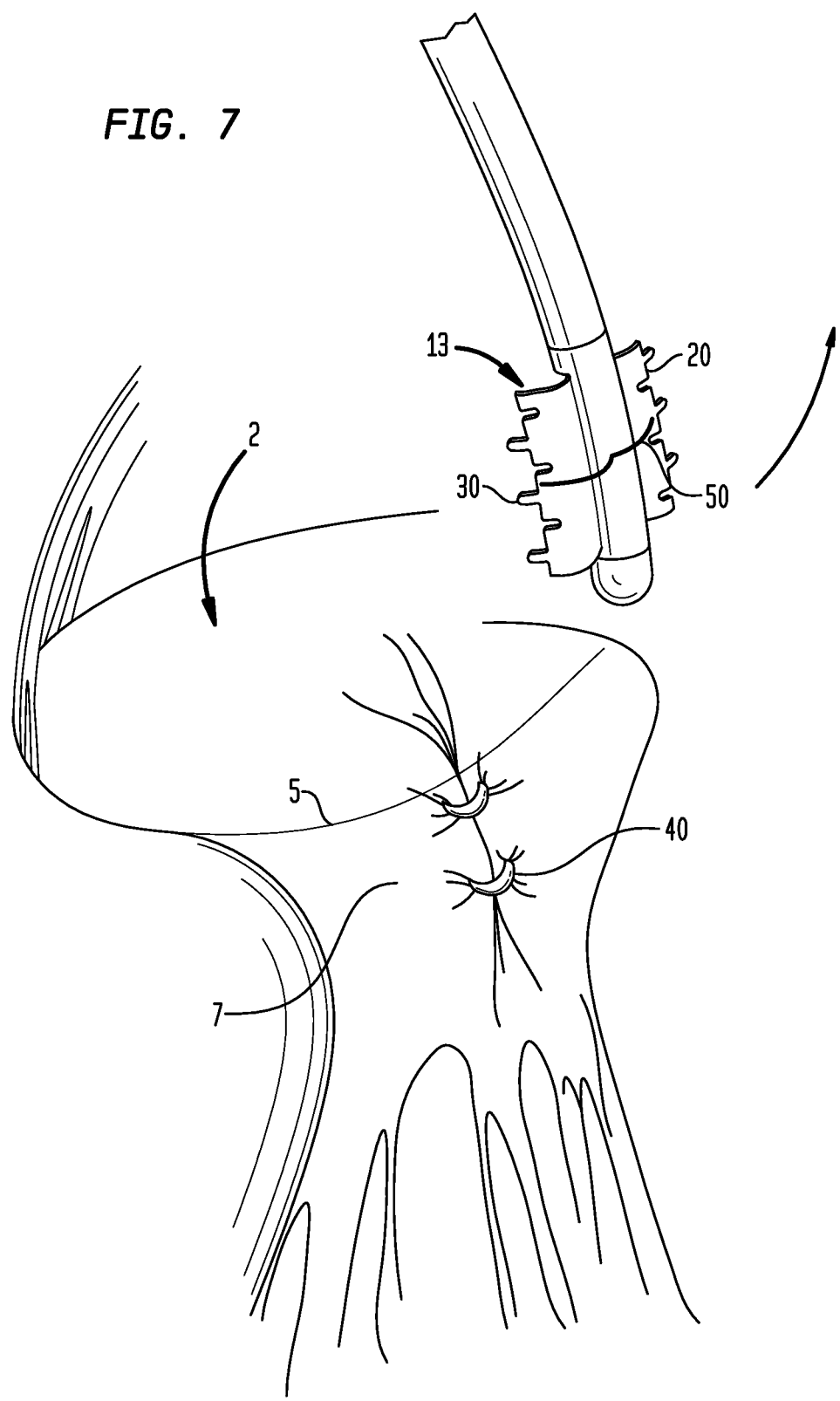

Referring to FIG. 7, once the clips 40 have been applied to the lower portion 7 of the posterior leaflet 2, the user may pull the deployment wire 50 proximally to move the doors 20 to a sufficiently open condition to allow the user to move the capture assembly 13 away from the posterior leaflet and disengage the prongs 30 of the doors 20 from the captured tissue 44.

After disengagement of the doors 20 from the posterior leaflet 2, the doors may be moved into the fully closed condition for withdrawal from the patient. To close the doors 20 after the clips 40 have been applied to the tissue, a memory feature may be included in the capture assembly 13 to provide a force according to its bias that tends to close the doors. Examples of such a memory feature may include a living hinge that couples the doors to the closed side 18 of the capture assembly 13 or a leaf spring 148, such as that shown in FIG. 8B. The procedure described above may be repeated to apply one or more additional clips 40 onto the same posterior leaflet 2.

Figure 8A:
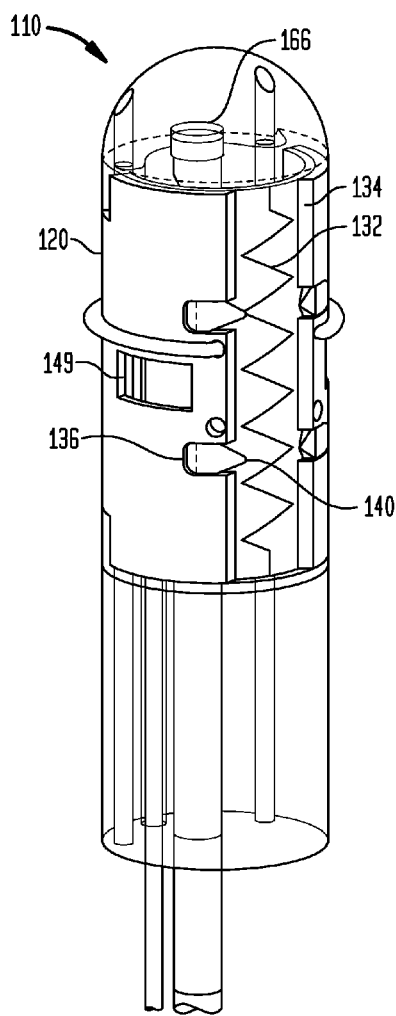
FIG. 8A is a perspective view of another embodiment of a device for gathering tissue of a heart valve leaflet, shown with the doors in the fully closed condition.
Figure 8B:
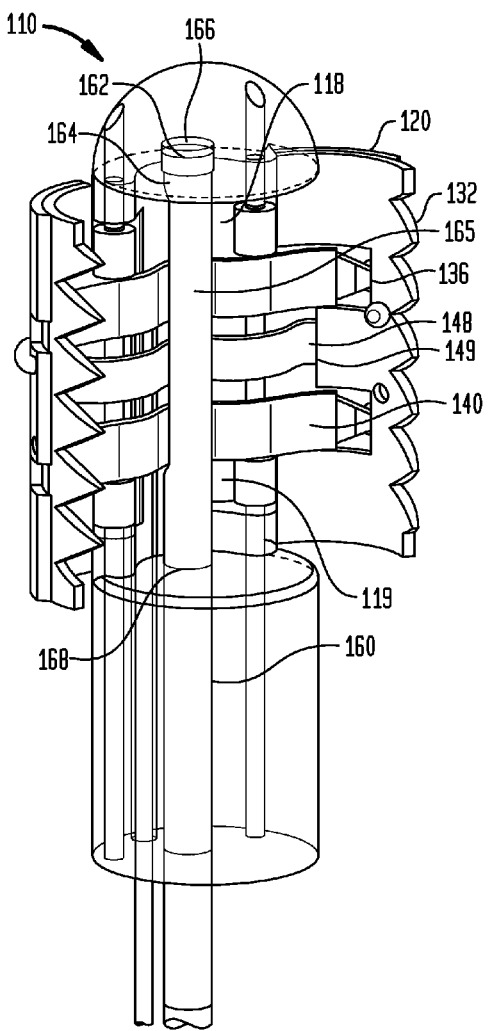
FIG. 8B is a perspective view of the device of FIG. 8A, shown with the doors in the fully open condition.

An alternative embodiment of a device 110 for gathering heart valve leaflet tissue is shown in FIGS. 8A and 8B. The device 110 is similar to the device 10 described above, but the device 110 includes alternate versions of the doors, the actuation rod, and the memory door-closing feature.

Rather than having doors with prongs and corresponding recesses at their free edge, the device 110 has doors 120 having a serrated edge 132. The serrated edges 132 of the doors 120 are adapted to become interleaved with one another when the doors are moved to the closed condition shown in FIG. 8A. The serrated edges 132 together define a longitudinal external recess 134 when the doors 120 are in the closed condition.

The actuation rod 160 of the device 110 is similar in function to the actuation rod 60 described above. The actuation rod 160 has a generally oval cross-section along its entire length, with the exception of an elongated portion 165 spaced from the distal end 162 of the actuation rod that has a substantially round cross-section that is smaller than the oval cross-section in at least one direction. As a result of this difference in cross-sections, a bump 164 is defined on the distal end 162 of the actuation rod 160 that extends farther in a lateral direction from the longitudinal axis of the actuation rod than the elongated portion 165. When the actuation rod 160 is in the initial position, the elongated portion 165 is disposed adjacent the clips 140. When the user slides the actuation rod 160 proximally, the bump 164 contacts the clips 140 and forces them toward the closed side 118 of the compartment 119, disengaging the clips from the slots 136.

The aperture 166 at the distal end of the compartment 119 and the aperture 168 at the proximal end of the compartment have oval shapes that correspond to the oval shape of the actuation rod 160. The matching of these oval shapes prevents the actuation rod 160 from rotating, thereby keeping it oriented with the bump 164 facing toward the clips 140.

The device 110 further includes a leaf spring 148 formed from a memory metal so as to be biased to the closed position shown in FIG. 8A. The ends of the leaf spring 148 are engaged in opposing slots 149 in the doors 120 so that the leaf spring provides a force according to its bias that tends to close the doors.

In the foregoing, particular structures have been described that are adapted to gather, secure, and repair heart valve leaflet tissue. The invention also contemplates the use of alternative structures for such purposes, including structures having different lengths, shapes, and configurations. For example, rather than capturing tissue by the movement of two opposing doors, only a single rotatable door may be used. In such a variant, the door maybe rotatably coupled to a first longitudinal edge of the closed side of the capture assembly, the closed side and the door in the closed condition collectively defining the tissue capturing compartment. During use of such a device, the single door may be closed against a second longitudinal edge of the closed side of the capture assembly to capture tissue of the heart valve leaflet inside the tissue capturing compartment. Other devices that have elements that rotate toward other rotatable or fixed structures to gather leaflet tissue into a fold or pleat onto which a clip may be applied are also contemplated herein.

Furthermore, although the devices have been described herein as including actuation rods with bumps that are moved proximally to displace the clips and release them for application to captured tissue, the invention is not limited to such structures. For example, in one variation thereof, the bump initially may be positioned adjacent the proximal end wall of the capture assembly, and the bump may be moved distally to displace the clips and release them for application to tissue captured in the tissue capturing compartment. In such an embodiment, the atraumatic tip of the device may have a through bore that accommodates the distal end of the actuation rod as it is moved distally. The distal end of the actuation rod may remain captured by the atraumatic tip throughout the entire travel motion of the rod, thereby minimizing any lateral deflection of the rod that may prevent the bump from displacing and releasing the clips during the clip deployment process. In another variation, one or more bumps of the actuation rod may initially be positioned facing away from the closed side of the capture assembly, and the actuation rod may be rotated to bring the bump or bumps into contact with the clips to displace and release them for application to tissue captured in the tissue capturing compartment.

Moreover, although the door-closing feature has been described above as a leaf spring, such as that shown in FIG. 8B, any structure may be used to provide a force according to its bias that tends to close the doors. For example, the doors and the closed side of the capture assembly may be constructed from a single contiguous piece of material, such as a memory metal or a strong, resilient metal or polymer, so as to provide a living hinge operable to bias the doors to the closed condition. Alternatively, a hinge such as that shown in FIG. 2C may include a coil spring disposed around the pin, the coil spring having an bias that tends to close the doors.

Although the devices herein have been described in connection with the application of two clips onto a posterior leaflet, the invention contemplates the application of only one clip or any number of clips greater than one to any leaflet tissue during a single insertion of the device into a patient. In that regard, the tissue capturing compartment may be sufficiently long to accommodate any reasonable number of clips in side-by-side relationship in the longitudinal direction of the compartment, and all or less than all of the retained clips may be applied in a single procedure.

Although the various delivery devices have been described herein in connection with tightening the posterior leaflet of a mitral valve, all of the delivery devices may be used to repair other heart valve leaflets, such as the anterior leaflet of the mitral valve, or any other tissue of the body for which a reduction in the length of the tissue would be beneficial.

Although the invention herein has been described with reference to particular embodiments in which the device is inserted into the patient and advanced to the mitral valve using a transseptal approach, it is to be understood that the invention contemplates embodiments in which the device reaches its target through another portion of the heart, such as the apex of the heart, through a portion of the vasculature of the patient, such as a subclavian artery, or through the aorta. In such embodiments, some of the device components may have to be oriented in a different direction than described herein. For example, the invention contemplates embodiments in which the capture assembly approaches the mitral valve from the downstream side as well as from the upstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present invention enjoys wide industrial applicability including, but not limited to, methods and devices for gathering tissue in a patient.

The invention claimed is:

1. A method of gathering tissue in a patient, the method comprising:
    inserting an elongated device into the patient to a position adjacent the tissue, the device including a capture assembly having a closed side and a door rotatable between an open condition and a closed condition, the closed side and the door in the closed condition collectively defining a tissue capturing compartment, the device including a clip coupled to the door and biased to move the door to the closed condition, the capture assembly includes a spring element coupled at the door and biased to move the door to the closed condition;
    moving the door from the closed condition to the open condition and engaging the door against the tissue;
    closing the door against the tissue to capture a portion of the tissue inside the tissue capturing compartment, the captured tissue being formed into a gathered configuration, the door being moved to the closed condition by the bias of the clip and the spring element; and
    applying the clip from the capture assembly to the captured tissue so as to hold the captured tissue substantially in the gathered configuration by releasing the clip from engagement with the door.

2. The method as claimed in claim 1, wherein the tissue is a heart valve leaflet.

3. The method as claimed in claim 1, wherein the door includes at least one prong projecting therefrom, and the closing step includes grasping the captured tissue with the at least one prong.

4. The method as claimed in claim 1, wherein the door includes a portion with serrations, and the closing step includes grasping the captured tissue with the serrations.

5. The method as claimed in claim 1, wherein the device includes a deployment element attached to the door and operable by a user, and the moving step includes pulling the deployment element to rotate the door to the open condition.

6. The method as claimed in claim 1, wherein the door is a first door, and the capture assembly includes a second door rotatable between open and closed conditions, and the closing step includes closing the first and second doors against the tissue to capture the portion of the tissue inside the tissue capturing compartment.

7. The method as claimed in claim 1, wherein the clip is biased toward a closed condition and is engaged with the door so that moving the door to the open condition moves the clip to an open condition, and the applying step includes releasing the clip from engagement with the door, whereby the clip moves from the open condition to the closed condition.

8. The method as claimed in claim 7, wherein the device includes an actuating rod movable relative to the at least one clip, and the applying step includes moving the actuating rod to contact the at least one clip and releasing the at least one clip for application to the captured tissue.

9. A device for gathering tissue in a patient, the device comprising:
    an elongated catheter having a proximal portion and a distal portion; and
    a capture assembly at the distal portion of the catheter, the capture assembly including a closed side and a door rotatable between an open condition and a closed condition, the closed side and the door in the closed condition collectively defining a tissue capturing compartment,
    the door being operable to capture a portion of the tissue in a gathered configuration within the tissue capturing compartment;
    a clip releasably held in the tissue capturing compartment and adapted to be applied to the captured tissue for holding the captured tissue in the gathered configuration, the clip being coupled to the door and biased to move the door to the closed condition; and
    a spring element coupled at the door and biased to move the door to the closed condition.

10. The device as claimed in claim 9, wherein the door has one edge rotatably connected to the closed side of the capture assembly and a free edge opposite the one edge, the free edge including at least one prong projecting therefrom.

11. The device as claimed in claim 9, wherein the door has one edge rotatably connected to the closed side of the capture assembly and a free edge opposite the one edge, the free edge including a plurality of serrations.

12. The device as claimed in claim 9, further comprising a deployment element attached to the door and extending through the elongated catheter.

13. The device as claimed in claim 9, wherein the door is a first door, and the capture assembly includes a second door rotatable between open and closed conditions, the first and second doors being operable to capture the portion of the tissue in the gathered configuration within the tissue capturing compartment.

14. The device as claimed in claim 9, wherein the clip is biased toward a closed condition and is engaged with the door so that moving the door to the open condition moves the clip to an open condition.

15. The device as claimed in claim 14, wherein the clip has a first end and a second end, and the door includes a slot, the first end of the clip being engaged in the slot.

16. The device as claimed in claim 15, wherein movement of the door to the open condition creates a biasing force in the clip tending to move the door to the closed condition.

17. A device as for gathering tissue in a patient, the device comprising:
    an elongated catheter having a proximal portion and a distal portion;
    a capture assembly at the distal portion of the catheter, the capture assembly including a closed side and a door rotatable between an open condition and a closed condition, the closed side and the door in the closed condition collectively defining a tissue capturing compartment, the door being operable to capture a portion of the tissue in a gathered configuration within the tissue capturing compartment;
    a clip releasably held in the tissue capturing compartment and adapted to be applied to the captured tissue for holding the captured tissue in the gathered configuration; and
    an actuating rod slidably disposed in the tissue capturing compartment, the actuating rod having a laterally projecting bump, and the clip being at least partially held in a travel path of the bump, whereby movement of the bump through the travel path causes the bump to release the clip for application to the captured tissue.

18. The device as claimed in claim 17, wherein the bump has an oval cross-section, and a portion of the actuating rod adjacent the bump has a round cross-section that is smaller than the oval cross-section in at least one direction.

* * * * *